United States Patent [19]
Laufer et al.

[11] Patent Number: 5,972,026
[45] Date of Patent: Oct. 26, 1999

[54] BRONCHIAL STENTER HAVING DIAMETRICALLY ADJUSTABLE ELECTRODES

[75] Inventors: Michael D. Laufer, Menlo Park; Keith M. Burger, San Francisco; Bryan E. Loomas, Saratoga; Donald A. Tanaka, San Jose, all of Calif.

[73] Assignee: Broncus Technologies, Inc., Mountain View, Calif.

[21] Appl. No.: 09/003,750

[22] Filed: Jan. 7, 1998

Related U.S. Application Data

[63] Continuation-in-part of application No. 08/833,550, Apr. 7, 1997.

[51] Int. Cl.$^6$ ...................................................... A61B 17/39
[52] U.S. Cl. ............................... 607/96; 607/101; 606/41
[58] Field of Search ................................ 607/96, 98–99, 607/101, 102, 122, 113; 606/41, 39

[56] References Cited

U.S. PATENT DOCUMENTS 5,103,804  4/1992  Abele et al. .
5,545,193  8/1996  Fleischman et al. .

Primary Examiner—Linda C. M. Dvorak
Assistant Examiner—Roy Gibson
Attorney, Agent, or Firm—Burns, Doane, Swecker & Mathis LLP

[57] ABSTRACT

A device and method for treating collapsed bronchial tubes found in patients with chronic obstructive pulmonary disease and asthma are provided. The device delivers energy so that the tissue is inductively heated by directing electromagnetic energy into the tissue. The device includes electrodes having adjustable diameters to enable the electrodes to contact the wall of the bronchial tubes. The method includes heating the bronchial tube to cause at least a portion of the cross links of the collagen in the wall to unlink/open and subsequently form new cross links after the collagen fibers have realigned. The procedure effectively reinforces the structural integrity of the wall and thereby prevents the lumen from collapsing.

13 Claims, 6 Drawing Sheets

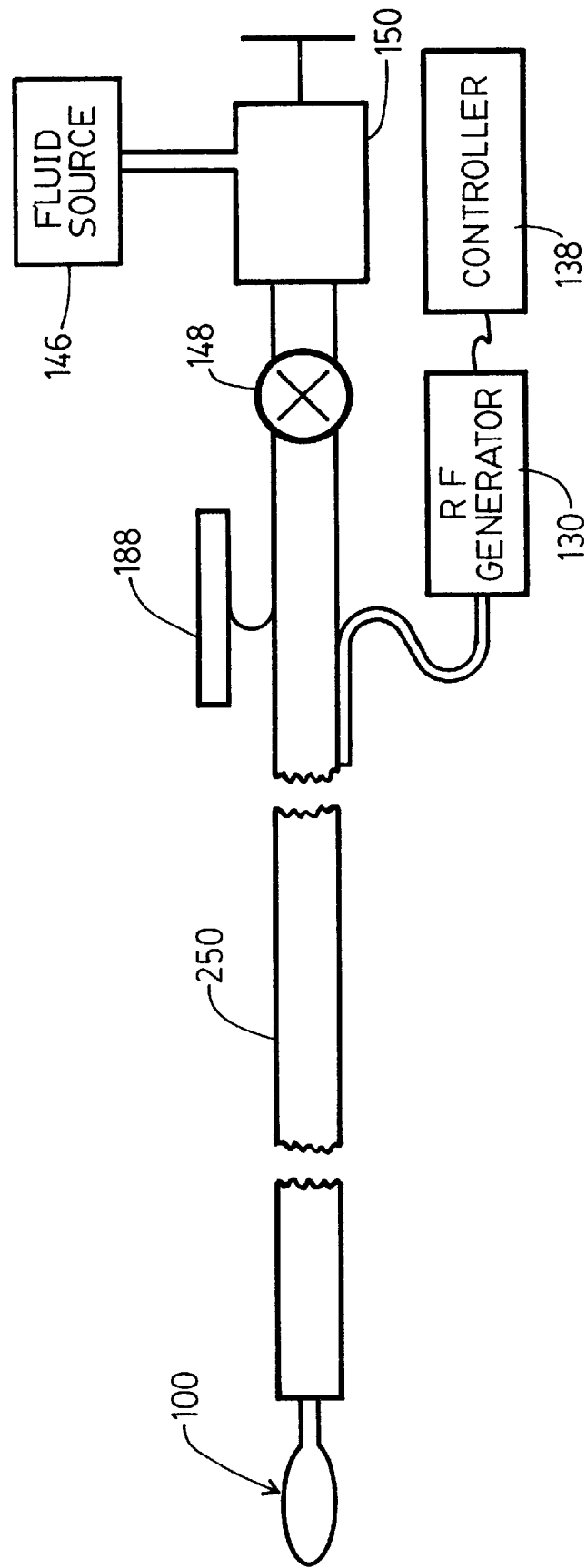
FIG._1A.

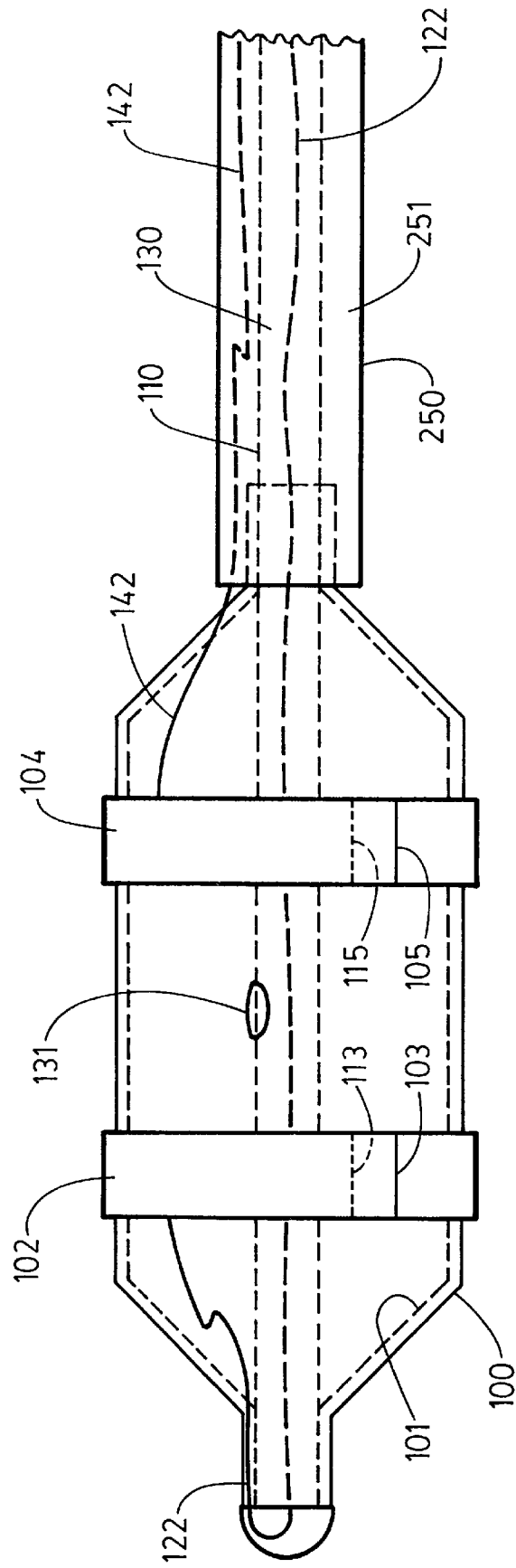
FIG._1B.

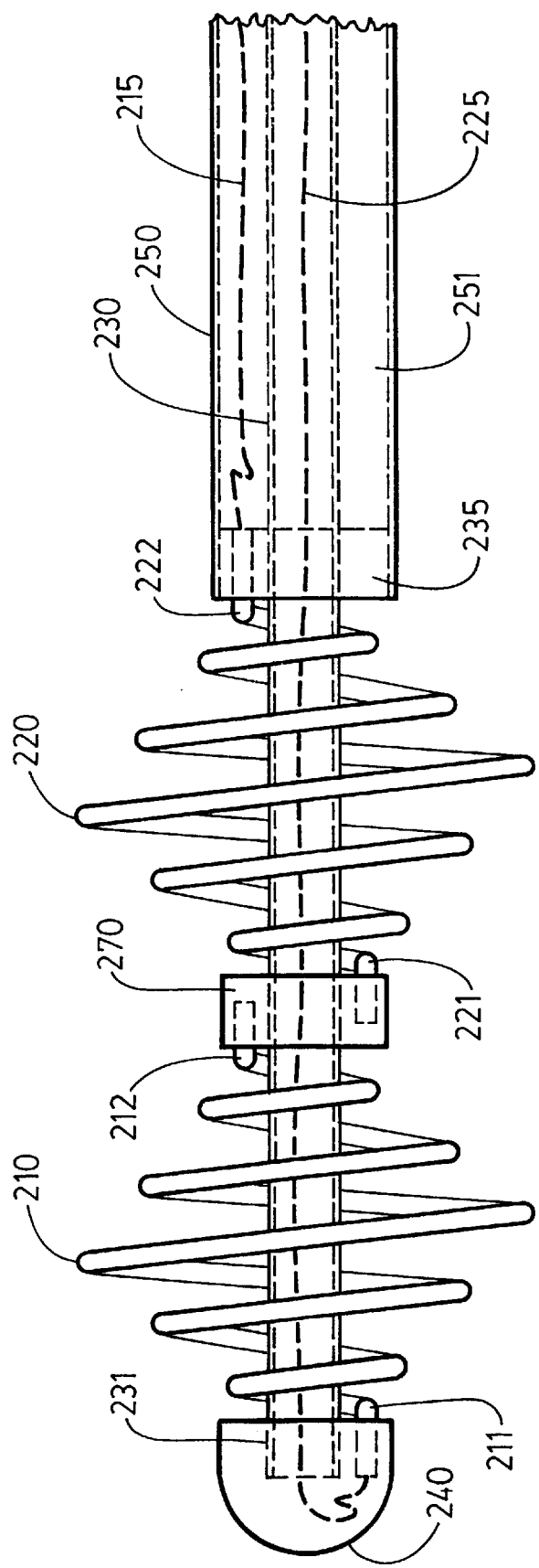
FIG._2.

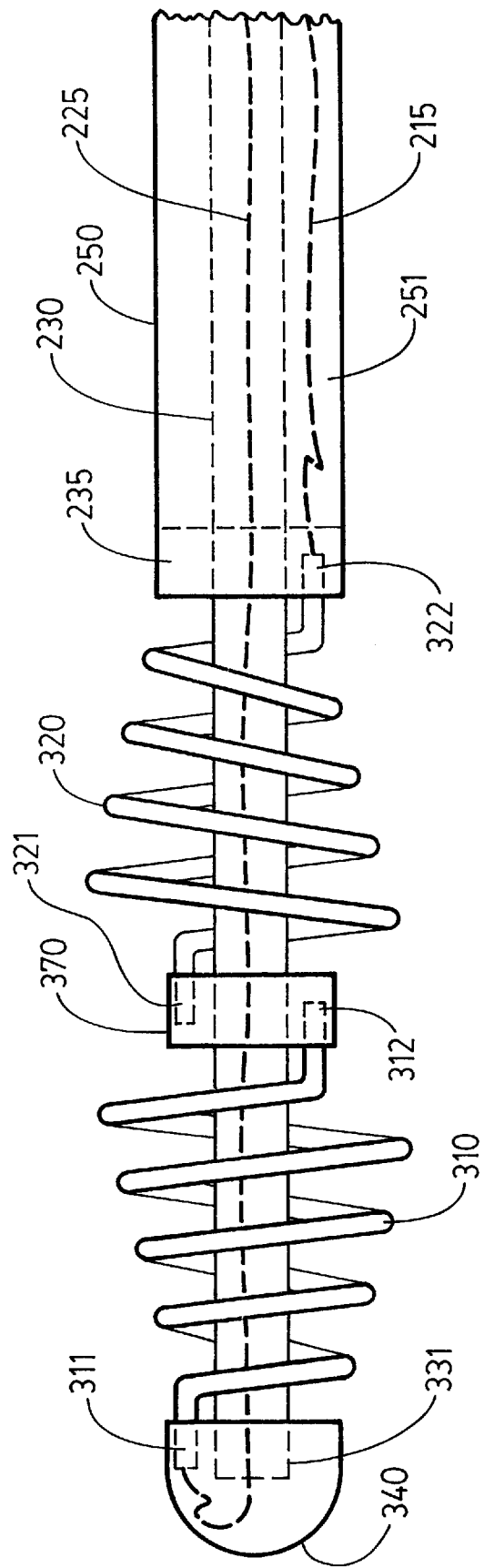
FIG._3.

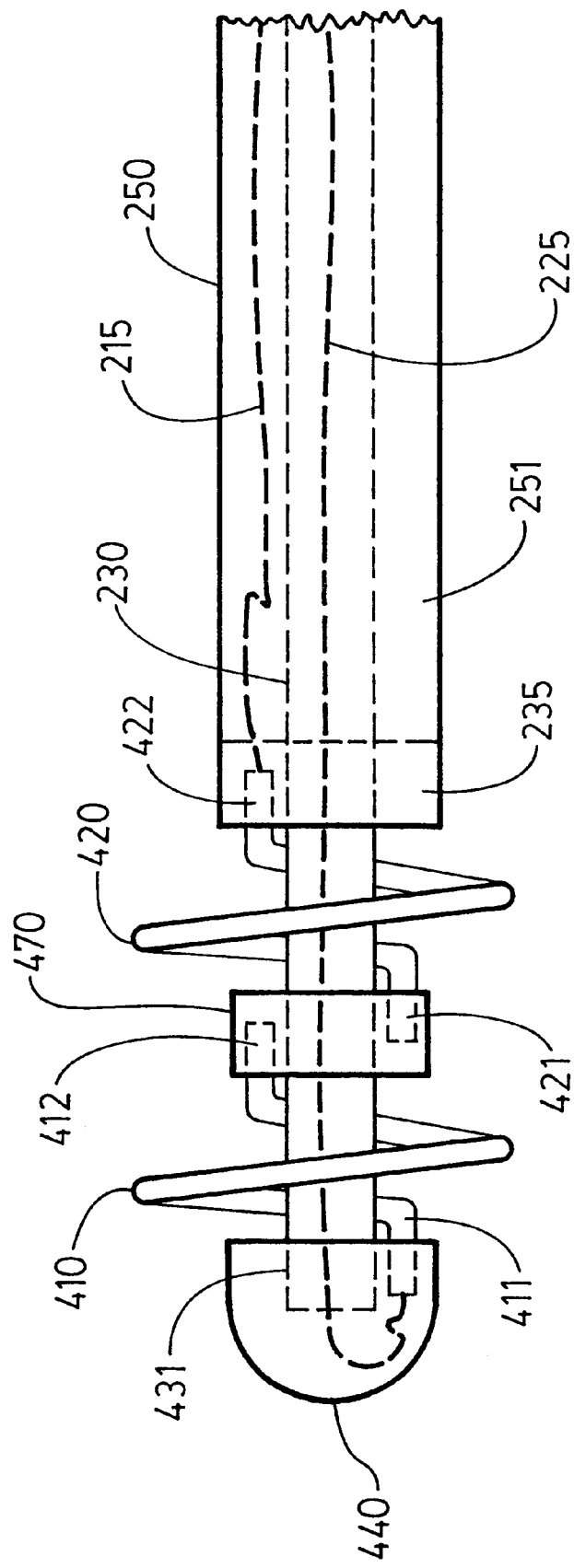
FIG._4.

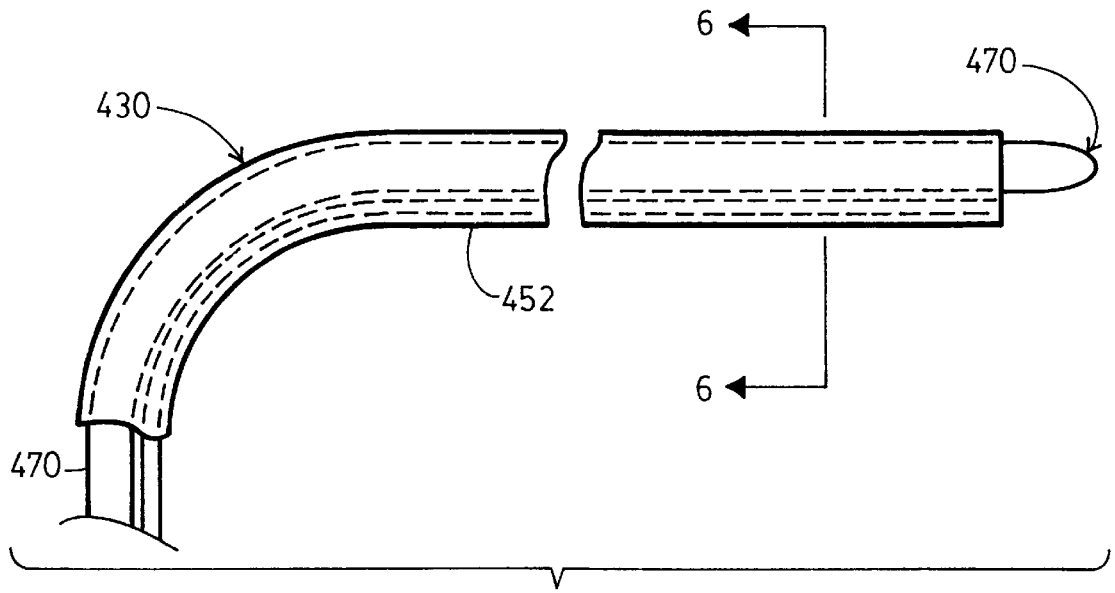
FIG._5.
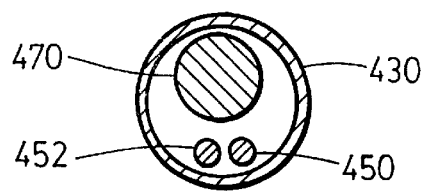
FIG._6.
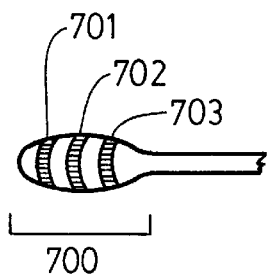
FIG._7.
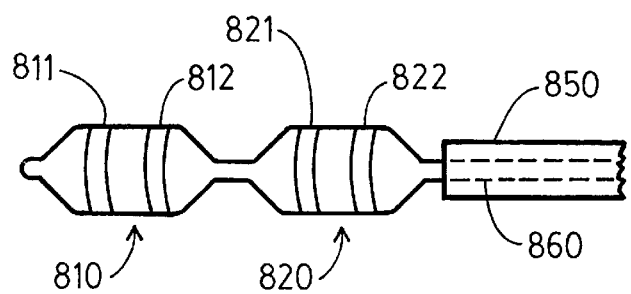
FIG._8.

BRONCHIAL STENTER HAVING DIAMETRICALLY ADJUSTABLE ELECTRODES

REFERENCE TO RELATED APPLICATION

This is a continuation-in-part application of application Ser. No. 08/833,550 filed on Apr. 7, 1997.

FIELD OF THE INVENTION

The present invention relates to a device and method for treatment of the airway obstruction found in chronic obstructive pulmonary diseases (COPD), such as cystic fibrosis, chronic bronchitis, emphysema, and asthma.

BACKGROUND OF THE INVENTION

Chronic obstructive pulmonary diseases (COPD), which includes such entities as cystic fibrosis, chronic bronchitis, and emphysema, are steadily increasing in frequency, possibly due to continued smoking, increasing air pollution, and the continued aging of the population. COPD is characterized by edema of the mucous membranes, which line the interior walls of the tracheobronchial tree. When the mucosa accumulates an abnormal quantity of liquid, the profuse and thickened serous fluid excreted may seriously affect ventilation in the alveoli. The mucus resists movement up the walls of the tracheobronchial tree, normally efficiently accomplished by the cilia throughout the airways which are also destroyed. Consequently, the serous fluid can form mucus plugs, which can shut off alveoli or entire airways. In addition to secretion accumulation, airway obstruction can occur because the tubes collapse due to destruction of connective tissue. This reduces the ability to get oxygen into the blood and carbon dioxide out of the blood.

Asthma is the most common form of bronchoconstrictive disease and pathologically involves constriction of the bronchioles, hypertrophy of the muscles of the bronchioles, and a characteristic infiltrate of eosinophils. Both asthma and COPD are characterized by the constriction or collapse of airway passages in the lungs that are not supported by cartilage. This condition is marked by labored breathing accompanied by wheezing, by a sense of constriction in the chest, and often by attacks of coughing and gasping. Individuals who are afflicted may attempt to compensate by blowing harder only to have the airways collapse further. A person with poor resulting ventilation suffers from a number of metabolic conditions including accumulation of carbon dioxide. These individuals also often have hyperinflated enlarged lungs and barrel-shaped chests.

A wide variety of drugs are available for treating the symptoms of COPD but none is curative. Cystic fibrosis, chronic bronchitis, and emphysema are typically treated with agents to thin and dry up the secretions and with antibiotics to combat infection and with bronchodilators. These drugs include potassium iodide, antihistamines, various antibiotics, beta agonists and aminophylline. Unfortunately, a large number of patients are not responsive to these medications or become non-responsive after prolonged periods of treatment. For severe cases involving collapsed air passages, surgeons have endeavored to alleviate this disabling condition by either removing a portion of the lungs or constricting the volume of lung available for respiration by stapling off sections thereof. The result is that functionally the diaphragm and muscles in the chest wall operate on a smaller lung volume which may improve air movement for some individuals. These operations are quite risky and are associated with a large number of deaths. Patients undergoing these treatments are quite ill and these procedures are considered final options.

Notwithstanding the conventional treatments available, there exists a need in the art for an effective treatment for chronic obstructive pulmonary diseases, such as cystic fibrosis, chronic bronchitis, emphysema and asthma. Specifically, there is a need for effective treatment for individuals with obstructed airway passages to restore pulmonary function which only requires minimal surgery.

SUMMARY OF THE INVENTION

Many types of tissue can be molded and remodeled to correct defects and dysfunction. One technique involves physical manipulation using mechanical instruments and/or balloons to effect selective shrinking, stretching, flattening, thinning or thickening in addition to changing the material properties of the tissue. These changes of properties include alteration of the elastic coefficient of the tissue causing it to be stiffer, changing the tensile strength of the tissue, changing the shear strength of the tissue, and changing the floppiness or resiliency of the tissue. When the tissue is close to the surface of the skin or part of a non critical organ, physical manipulation is feasible and can be executed with minimal trauma to the patient. However, when the tissue is in an internal organ, in particular, in the lungs or other vital organ, molding and remodeling by physical manipulation can involve complicated and often risky surgery.

The present invention is based, in part, on the development of heat treatment apparatuses having diametrically adjustable electrodes that are capable of delivering energy to bronchial tubes uniformly. The heat is preferably inductively applied by directing electromagnetic energy, such as radio frequency, into the tissue. The invention also provides for a method for treating a bronchial tube which comprises the steps of:

a) maneuvering a heating device into the lumen of the bronchial tube;

b) heating the tissue of the bronchial tube to cause collagen in the wall of the lumen to undergo a structural transformation effective to render the wall capable of supporting the lumen without collapsing; and c) removing the device from the patent's bronchial tube.

Prior to treatment, the lumen can be non-collapsed, partially, or fully collapsed. Preferably, the bronchial tube is heated to a temperature in the range between about 60° C. and about 95° C. for about 0.1 to about 600 seconds. With the inventive procedure, extensive surgery and the accompanying trauma are avoided.

This invention is particularly useful for treating subjects experiencing difficulty in breathing as a result of obstructed airway passages caused by, for example, chronic obstructive pulmonary disease, including, for example, cystic fibrosis, chronic bronchitis, emphysema, and asthma. This invention ameliorates the affects of these diseases by improving lung function by keeping the airway passages open. Specifically, the present invention provides a device and method for effecting changes in collagen-containing soft tissue in the bronchial tubes or air passages of the lungs which have collapsed. The causes of the collapse may be the destruction of the connective tissue, the disease process, swelling, and/or muscle-dependant constriction. The invention is directed to a treatment process which effectively creates an internal bronchial stent which prevents the air passages from collapsing. As used herein, the term "bronchial tube" or "air passage" refers to the sub-segments that branch from the main stem bronchus of the lungs. The term "collapsed lumen" refers to a condition of lumen of a bronchial tube wherein the lumen is occluded to the extent that substantial blockage of air flow through the lumen exists. The diameter of a non-collapsed lumen may be substantially equal to that of a normal bronchial tube or may be less as in the case of a partially collapsed but functional lumen. It is understood that the term "collapsed lumen" encompasses partially collapsed lumens. Cartilage is not present around these air passages in appreciable amounts so they have little intrinsic supportive structures.

In one aspect, the invention is directed to an apparatus, for treating a bronchial tube having a lumen, which includes:

(a) a treatment device comprising at least one balloon that is attached to a the treatment device wherein each balloon inflates upon the injection of a fluid into the balloon and each balloon has at least one electrode that is attached thereto and which when energized causes collagen in the wall of the lumen to undergo a structural transformation effective to render the wall capable of supporting a non-collapsed lumen;

(b) a source of fluid;

(c) a source of energy; and (d) means for transmitting energy from the source of energy to the at least one electrode.

In another aspect, the invention is directed to an apparatus, for treating a bronchial tube having a lumen, which includes:

(a) a treatment device comprising at least one balloon that is attached to a the treatment device wherein each balloon inflates upon the injection of a fluid into the balloon and each balloon has at least one electrode that is attached thereto and which when energized causes collagen in the wall of the lumen to undergo a structural transformation effective to render the wall capable of supporting a non-collapsed lumen;

(b) a source of fluid;

(c) a source of energy; and (d) means for transmitting energy from the source of energy to the at least one electrode.

BRIEF DESCRIPTION OF THE DRAWINGS

As used herein, like reference numerals will designate similar elements in the various embodiments of the present invention wherein:

FIGS. 1A and 1B show an embodiment of the heat treatment apparatus of the present invention which employs electrodes positioned on the outer surface of a balloon, FIG. 1B is an enlarged view of the distal end of the device shown in FIG. 1A;

FIGS. 2, 3, and 4 show embodiments of the heat treatment apparatus which employ diametrically adjustable electrodes;

FIGS. 5 and 6 are cross-sectional views of a bronchoscope with a heat treatment apparatus device positioned therein; and FIG. 7 shows an embodiment of the heat treatment apparatus with multiple electrodes; and FIG. 8 shown an embodiment of the heat treatment apparatus with multiple balloons.

DETAILED DESCRIPTION OF THE PREFERRED EMBODIMENTS

FIGS. 1A and 1B shows an embodiment of the heat treatment apparatus which includes balloon 100 that is positioned at or near the distal end of elongated rod 110 which is positioned within the lumen or aperture 251 of catheter sheath 250. It is understood that the term "rod" also encompasses tubes which have hollow channels. As shown, the balloon with inner surface 101 is in the inflated state having been inflated with an appropriate fluid such as air or saline that is injected from conduit 130 and into the interior of the balloon through aperture 131 in the rod. The apparatus includes electrodes 102 and 104 which are spaced apart along the outer perimeter of the inflated balloon. It is understood that the number of electrodes and their configurations on the outer surface of the balloon can be varied. These electrodes come into contact with the wall of the lumen when the balloon is inflated. The electrodes employed in the present invention can have different configurations. For example, the electrodes can be conventional coil wires with round cross sections, or they can have a non-round configuration, such as, for example, a thin, foil or band with a rectangular cross section. For the device shown in FIG. 1B, electrodes 102 and 104 are preferably flat bands each extending around the circumference of the balloon. To permit expansion of the balloon, each band is positioned around the outer surface of the balloon with the two ends overlapping each other. As shown the FIG. 1B, electrode 102 is a band having ends 103 and 113 with a portion of the band adjacent to end 103 overlapping a portion of the band adjacent to end 113. Similarly, electrode 104 is a band having overlapping ends 105 and 115.

Balloons suitable for the present invention may be of similar material and design as those currently being used in percutaneous transluminal angioplasty. For a review of the state of the art, see U.S. Pat. Nos. 4,807,620; 5,057,106; 5,190,517; 5,281,218; 5,314,466; 5,370,677; 5,370,678; 5,405,346; 5,431,649; 5,437,664; 5,447,529; and 5,454,809 all incorporated herein by reference. The balloon is preferably fabricated of a non-elastic material that is substantially impermeable to the fluid. In this fashion, the balloon can be designed to have a more uniform cross section and a fixed maximum diameter when the balloon is fully inflated. This provides better contact of the electrodes to the wall of the bronchial tube. Suitable non-elastic materials include, for example, polyester (e.g., MYLAR) and polyethylene. When the balloon is fully inflated, the length of its diameter is preferably 1 mm to 300 mm, and more preferably about 3 mm to 5 mm.

It is understood that the balloon can also be made of elastic material such as silicone, natural latex, and polyethylene. With elastic material balloons, the degree of expansion is proportional to the amount of force introduced into the interior of the balloon. Moreover, the balloon preferably will substantially return to its original, non-expanded form when the internal force is released.

The balloon of the heat treatment apparatus is preferably constructed of non-elastic material that is initially folded and/or collapsed. In this non-inflated state, the diameter of the balloon is small enough that the balloon can be positioned inside an aperture or working channel of a bronchoscope. In use, the bronchoscope first is positioned at the treatment site before the balloon to exposed and then inflated. Heat treatment is then commenced.

The present invention is based in part on the discovery that the structural integrity of bronchial tubes, especially those which do not have significant amounts of cartilage present, can be significantly recreated by subjecting the bronchial tubes to a sufficient amount of heat to cause at least a portion of the cross links of the collagen fibers to open and subsequently form new cross links after the collagen fibers have realigned thereby causing the tubes to remain patent. This procedure changes the structure of the integral collagen and the shape of the tube.

FIGS. 1A and 1B show that electrodes 102 and 104 are connected via cables 122 and 142, respectively, to a radio frequency (RF) generator 130 with controls 138. Rod 110 is also connected to syringe 150 which is employed to inject a fluid from source 146 through valve 148 into the balloon.

The frequency range of RF radiation useful in the present invention is typically about 10 KHZ to about 100 MHZ, preferably in the range of about 200 KHZ to about 800 KHZ. However, frequencies outside this range may be used at the discretion of the operating surgeon. Typically, the amount of power employed will be from about 0.01 to 100 watts and preferably in the range of about 1 to 25 watts. Alternatively, alternating current or microwave radiation typically in the frequency range of about 1,000 MHz to about 2,000 MHz and preferably from about 1,100 MHZ to about 1,500 MHz may be used in place of RF radiation. In the latter case, the RF generator 130 is replaced with a microwave generator, and the cables 122 and 142 are replaced with waveguides.

In use, after the operating surgeon has placed the heat treatment apparatus within the lumen of a bronchial tube to be treated, the balloon is first exposed and then inflated with fluid from syringe 150 located conveniently for the surgeon. In the case where the lumen of the bronchial tube has collapsed or is partially collapsed, the balloon is preferably inflated until the lumen has expanded to its normal diameter with the balloon in substantial contact with the inner surface of the lumen. Alternatively, in the case where the lumen has not collapsed, the balloon is preferably inflated until it is in substantial contact with the inner surface of the lumen. Indeed, only minimum inflation of the balloon may be necessary in treating a non-collapsed bronchial lumen which has a diameter that is about equal to, or less than that of the outer surface of the uninflated balloon.

The amount of inflation of the balloon is determined by the operating surgeon who monitors the balloon expansion by means of endoscopy or by other suitable imaging methods of the art. Generally, the heat required is induced in the tissue of the bronchial tube wall by the RF or microwave radiation emitting from the electrodes. The RF or microwave energy would be applied while observing for changes via simultaneous endoscopy, or other suitable imaging methods of the art.

As is apparent, the inventive heat treatment apparatuses can be employed to treat a bronchial tube regardless of whether its lumen has collapsed or not. Specifically, the devices can be used to treat bronchial tubes that have not collapsed, are partially collapsed, or are fully collapsed. Moreover, bronchial tubes may exhibit different degrees of closure depending on the state of respiration. For example, a bronchial tube may have a fully expanded lumen after inhalation but partially or completely closed during exhalation.

FIG. 2 shows another embodiment of the inventive heat treatment apparatus which includes a pair of electrode coils 210 and 220 that are positioned in tandem. The number of electrode coils is not critical. The apparatus also includes an elongated rod 230 which has a distal end 231 that is connected to a tip or knob 240 and has a proximal end which is at least partially slidably positioned inside aperture 251 of catheter sheath 250 that includes end coupler 235. Coil 210 has two ends, the first end 211 being attached to knob 240 and the second end 212 is attached to rotatable or floating coupler 270. Similarly, coil 220 has two ends, the first end 221 is attached to rotatable coupler 270 and the second end 222 is attached to end coupler 235.

As shown in FIG. 2, the coils are in the relaxed state which is meant that no torque is being applied to either coil. In this state, each coil has a "barrel" configuration so that the diameter of the outer contour formed by each coil is largest at its center and smallest at its two ends. A number of preferred methods can be employed to change the diameters of the contour. One method is to compress or expand the coils along the axis. For example, by pushing rod 230 outward so that knob 240 extends away from catheter sheath 250, the coil diameters will decrease. Another method of changing the diameter is to apply torque to the coils. Torque can be applied by rotating the rod in a clockwise or counterclockwise direction while keeping end coupler 235 stationary, e.g., attached to the inner surface of catheter sheath. Torque can also be applied by keeping rod 230 stationary while rotating end coupler 235. Alternatively, torque can be applied by rotating the rod in one direction while rotation end coupler 235 in the opposite direction. During the rotation process, rotatable coupler 270 will also rotate to thereby transfer torque from one coil to the other.

In practice, applying torque to adjust the radial diameters of the coils is preferred over compressing or pulling the coils lengthwise since applying torque creates less of a gradient in the diameter of each coil. According, preferably, the treatment apparatus is constructed so that end coupler 235 remains stationary. Torque is preferably applied by manually rotating rod 230. When more than one coil is employed, a rotatable coupler is required to connect adjacent coils. Multiple coil configurations are preferred over one with a single coil that has the same length (in the relaxed state) as the sum of the lengths of the smaller coils since the diameters of the smaller coils will tend to be more uniform and in contact with the wall of the bronchial tube being treated. Each coil in the embodiment shown in FIG. 2 is connected to an appropriate source of energy. For example, coils 210 and 220 can be connected by lines 215 and 225 to a radio frequency generator 130 as shown in FIG. 1A.

In operation, the heat treatment apparatus is positioned at the treatment site before the diameters of the coils are adjusted by applying torque. Energy is then applied to the coils.

FIGS. 3 and 4 show embodiments of the inventive heat treatment apparatus that are similar to the one of FIG. 2. The apparatus of FIG. 3 includes a pair of electrode coils 310 and 320 that are positioned in tandem. The apparatus also includes an elongated rod 230 which has a distal end 331 that is connected to a tip or knob 340 and has a proximal end which is at least partially slidably positioned inside aperture 251 of catheter sheath 250 that includes end coupler 235. Coil 310 has two ends, the first end 311 being attached to knob 340 and the second end 312 is attached to rotatable coupler 370. Similarly, coil 320 has two ends, the first end 321 is attached to rotatable coupler 370 and the second end 322 is attached to end coupler 235. As is apparent, each electrode has a cone-shaped contour and comprises a coil that is wound about and along the axis of the rod 230 and which in the relaxed state has a large diameter at one end and a small diameter at the other end.

The apparatus of FIG. 4 includes a pair of electrode coils 410 and 420 that are positioned in tandem. The apparatus also includes an elongated rod 230 which has a distal end 431 that is connected to a tip or knob 440 and has a proximal end which is at least partially slidably positioned inside aperture 251 of catheter sheath 250 that includes end coupler 235. Coil 410 has two ends, the first end 411 being attached to knob 440 and the second end 412 is attached to rotatable coupler 470. Similarly, coil 420 has two ends, the first end 421 is attached to rotatable coupler 470 and the second end 422 is attached to end coupler 235. As is apparent, each electrode has a single loop configuration that comprises a coil that is wound once about the rod 230. In this configuration, the two electrodes when in the relaxed state preferably form loops having the same diameter.

The devices of FIGS. 3 and 4 operate in essentially the same manner as the device of FIG. 2. Specifically, the same methods can be employed to adjust the radial diameter of the coils by compressing or pulling the coils or by applying torque to the coils. In addition, each coil is connected to an appropriate source of energy. For example, coils 210 and 220 can be connected by lines 215 and 225 to a radio frequency generator 130 as shown in FIG. 1A.

The electrodes employed in the present invention are constructed of a suitable current conducting metal or alloys such as, for example, copper, steel, and platinum. The electrodes can also be constructed of a shape memory alloy which is capable of assuming a predetermined, i.e., programmed, shape upon reaching a predetermined, i.e., activation, temperature. Such metals are well known in the art as described, for example, in U.S. Pat. Nos. 4,621,882 and 4,772,112 which are incorporated herein. For the present invention, the shape memory metal used should have the characteristic of assuming a deflection away (i.e., expands) from the elongated rod when activated, i.e., heated in excess of the normal body temperature and preferably between 60° C. and 95° C. A preferred shape memory alloy is available as NITINOL from Raychem Corp., Menlo Park, Calif. For the heat treatment apparatuses that employ coils as shown in FIGS. 2–4, preferably the electrodes are constructed of NITINOL in a predetermined shape and in the alloy's super elastic phase which can withstand very large deflections without deformation.

The above embodiments illustrate systems that employ bipolar electrodes. In each system, the electrodes emit RF energy with one conductive element acting as the active electrode and the other acting as the return electrode, or vice versa. One electrode would be connected to the positive electrode of the generator and the other would be connected to the negative electrode. An insulator is located between the conductive elements. In general, when operating in the bipolar mode, electrodes that have different polarities are electrically insulated from each other.

When the heat treatment device with the bipolar electrodes is positioned inside the lumen of a bronchial tube, activation of the RF generator causes collagen containing tissue in the lumen wall to increase in temperature. The particular heat pattern in the tissue will depend on the path of the electric field created.

Alternatively, heat treatment apparatuses employing a unipolar electrode can also be employed. For instance, in the case of the embodiment shown in FIGS. 1A and 1B, the heating device can have one or more inner electrodes 102 and/or 104 on the balloon surface and an outer or external electrode 188 that has a much larger surface area than that of the internal electrode(s) and that is placed on the outer surface of the patient's body. For example, the external electrode can be an external metal mesh or solid plate that is placed on the skin. Both the internal and external electrodes are connected to an RF generator which produces an electric field at a high frequency within the balloon. Because the collective surface area of the internal electrode(s) is much smaller than that of the outer electrode, the density of the high frequency electric field is much higher around the internal electrode(s). The electric field reaches its highest density in the region near the internal electrode(s). The increased density of the field around the internal electrode(s) produces localized heating of the tissue.

The function of the treating element, i.e., electrodes, is to apply a sufficient amount of energy to the walls of air passages to cause collagen in the walls to undergo a structural transformation to create more rigid walls that can support a non-collapsed, patent lumen. RF energy is no longer applied after there has been sufficient transformation, e.g., shrinkage, of the collagen fibers which may be gauged by removing the heating device from the treatment site and visually determining whether the lumen remains noncollapsed. Sufficient shrinkage may also be detected by fluoroscopy, external ultrasound scanning, pulse-echo ultrasound scanning, sensing the collapsing or straightening of the heating element with appropriate feedback variables, impedance monitoring or any other suitable method.

Substantial transformation may be achieved very rapidly, depending upon the specific treatment conditions. Because the transformation can proceed at a rather rapid rate, the RF energy should be applied at low power levels. Preferably, the RF energy is applied for a length of time in the range of about 0.1 second to about 600 seconds, and preferably about 5 to about 60 seconds. Suitable RF power sources are commercially available and well known to those skilled in the art. In one embodiment the RF generator employed has a single channel, delivering approximately 1 to 100 watts, preferably 1 to 25 watts, and most preferably 2 to 8 watts of RF energy and possessing continuous flow capability. The rate of collagen transformation can be controlled by varying the energy delivered to the heating element. Regardless of the source of energy used during treatment, the lumen or the bronchial tube is maintained at a temperature of at least about 60° C., preferably between 60° C. to 95° C. and more preferably between 70° C. to 85° C.

As is apparent, the heat treatment device of the present invention can comprise more than one electrode that is positioned at or near the distal end of the elongated rod. For example, FIG. 7 depicts schematically the distal end 700 of a heat treatment device which comprises electrodes 701, 702, and 703. In this configuration if the device operates in the bipolar mode, two of the three electrodes (e.g., 701 and 702) are connected to one pole of the RF generator and the other electrode (702) is connected to the other pole. Heat will be generated in the tissue adjacent the region between electrodes 701 and 702 and the region between electrodes 702 and 703. These electrodes 701, 702, and 703 can be attached to the exterior surface of a balloon, alternatively they represent adjustable coils in embodiments that do not require a balloon.

When the heat treatment device includes multiple electrodes, not all the electrodes need to be activated at the same time, that is, different combinations of electrodes can be employed sequentially. For example, in the case of the above described bipolar embodiment with three electrodes, electrodes 701 and 702 can be first activated to heat a section of the bronchial tube wall. During the heat treatment, electrode 703 can also be activated so that a second section of the bronchial tube wall is heat treated simultaneously. Alternatively, electrode 701 is disconnected to the RF generator before electrode 703 is activated so that the second section is treated subsequent to treatment of the first section.

In addition, when a heat treatment device includes multiple electrodes, the device can operate in the monopolar, bipolar mode, or both modes at the same time. For instance, electrodes 701 and 702 can be designed to operate in the bipolar mode while electrode 703 is designed to operate in the monopolar mode. As a further variation, the electrodes can be constructed of different materials and/or constructed to have different configurations. For example, electrode 701 can be made of a shape memory alloy and/or it can be a coil while each of the other electrodes 702 and 703 can be made of a non-shape memory material and/or it can be a band with a rectangular cross section.

The heat treatment device of the present invention can comprise more than one balloon that is attached to the elongated rod. For example, FIG. 8 depicts schematically the distal end of a heat treatment device which comprises balloons 810 and 820. Electrodes 811 and 812 are attached to the exterior surface of balloon 810 and electrodes 821 and 822 are attached to the exterior surface balloon 820. The device includes an elongated rod 860 which is positioned with the lumen of catheter sheath 850. This device is preferably constructed in the same manner as the device shown in FIG. 1B except for the additional balloon. Operation of the device is also similar although the surgeon has the choice of activating both sets of electrode simultaneously or one set at a time.

When treating a person with obstructed air passages, a preliminary diagnosis is made to identify the air passages or bronchial tube that can be treated. In treating a particular site, excessive fluid is first removed from the obstructed air passage by conventional means such as with a suction catheter. Thereafter, the inventive heat treatment device is maneuvered to the treatment site. Depending on the diameter of the lumen of the bronchial tube, the device can be positioned directly at the treatment site or it can be positioned into place with a bronchoscope. The elongated rod and outer catheter of the device are made of a flexible material so that it can be maneuvered through a bronchoscope. A bronchoscope is a modified catheter which is an illuminating instrument for inspecting and passing instruments (e.g., the treatment device) into the bronchial tubes.

FIGS. 4 and 5 illustrate a bronchoscope 430 having a heat treatment apparatus 470 slidably positioned within a lumen. The device also includes an image-transmitting fiber 450 and illuminating fiber 452. Any conventional bronchoscope with an appropriately sized and directed working lumen may be employed. The image transmitting fiber collects light from the distal end of the treating apparatus and directs the light to a viewing apparatus (not shown) for displaying an image of the obstructed air passage. The bronchoscope may have a panning system which enables the tips to be moved in different directions.

In operation, the bronchoscope is advanced from the person's nasal or oral cavity, and through the trachea, main stem bronchus, and into an obstructed air passage. The heat treatment apparatus is advanced forward from the bronchoscope to expose the tip containing the treatment device before the treatment device is energized. Depending on the size of the treatment device, the treatment device can be moved to another position for further heat treatment of the air passage. This process can be repeated as many times as necessary to form a series of patency bands supporting an air passage. This procedure is applied to a sufficient number of air passages until the physician determines that he is finished. As is apparent, the procedure can be completed in one treatment or multiple treatments. After completion of the treatment, energy is discontinued and the treatment device is removed from the patient.

The heating apparatus can be made to provide protection against overheating of the connective tissue which will cause the collagen to denature. Temperature monitoring and impedance monitoring can be utilized in a system which provides feedback to the user in the form of sounds, lights, other displays or which shuts down the application of energy from the heating element to the treatment site when sufficient transformation is detected and to avoid burning of the treatment site. The amount of energy applied can be decreased or eliminated manually or automatically under certain conditions. For example, the temperature of the wall of the air passage, or of the heating element can be monitored and the energy being applied adjusted accordingly. The surgeon can, if desired, override the feedback control system. A microprocessor can be included and incorporated into the feedback control system to switch the power on and off, as well as to modulate the power. The microprocessor can serve as a controller to monitor the temperature and modulate the power.

The invention is also directed to the demonstration or instruction of the inventive surgical techniques including, but not limited to, written instructions, actual instructions involving patients, audio-visual presentations, animal demonstrations, and the like.

While several particular embodiments of the invention have been illustrated and described, it will be apparent that various modifications can be made without departing from the spirit and scope of the invention. Accordingly, it is not intended that the invention be limited, except as by the appended claims.

What is claimed is:

1. An apparatus, for treating a bronchial tube having a lumen, which comprises:

a treatment device that comprises at least one radially adjustable electrode;

means for applying force to the at least one radially adjustable electrode to change the diameter of the at least one electrode;

a source of energy;

means for transmitting energy from the source of energy to the at least one electrode;

wherein the treatment device comprises an elongated rod that has a distal end, wherein the at least one radially adjustable electrode comprises a wire that is wound about and along a longitudinal axis of the elongated rod and which has a first end and a second end, wherein the first end is connected to the distal end of the elongated rod; and wherein the wire defines a barrel configuration with a center having a first diameter and two ends having second and third diameters and wherein the first diameter is larger than that of the second diameter and of the third diameter.

2. The apparatus of claim 1 wherein the means for applying force applies torque to the at least one radially adjustable electrode to change the electrode diameter.

3. The apparatus of claim 1 wherein the means for applying force changes the axial length of the at least one radially adjustable electrode.

4. The apparatus of claim 1 wherein the means for applying force applies torque to the at least one radially adjustable electrode to change the electrode diameter and changes the axial length of the at least one radially adjustable electrode.

5. An apparatus for treating a bronchial tube having a lumen, which comprises:

a treatment device that comprises at least one radially adjustable electrode;

means for applying force to the at least one radially adjustable electrode to change the diameter of the at least one electrode;

a source of energy;

means for transmitting energy from the source of energy to the at least one electrode; and an elongated rod that has a distal end and a proximal end and a longitudinal axis, wherein the treatment device comprises a plurality of electrodes that are designated the first electrode, and second electrode, and that are positioned in tandem so that the first electrode is attached to the distal end of the elongated rod, wherein each electrode comprises a wire that is wound about and along the longitudinal axis of the elongated rod and each electrode has a first end and a second end, with the proviso that when the number of electrodes is two, the treatment device includes a rotatable coupler which is attached to the second end of the first electrode and to the first end of the second electrode, and with the further proviso that when the number of electrodes is three or more, the electrodes are designated from one to n, and the first end of the electrode one is connected to the distal end of the elongated rod and the second end of the electrode n is connected to an end coupler, and each of the remaining electrodes is connected to an adjacent electrode by a rotatable coupler.

6. An apparatus, for treating a bronchial tube having a lumen, which comprises:

a treatment device that comprises at least one radially adjustable electrode;

means for applying force to the at least one radially adjustable electrode to change the diameter of the at least one electrode;

a source of energy;

means for transmitting energy from the source of energy to the at least one electrode;

wherein the treatment device comprises an elongated rod that has a distal end, wherein the at least one radially adjustable electrode comprises a wire that is wound about and along a longitudinal axis of the elongated rod and which has a first end and a second end, wherein the first end is connected to the distal end of the elongated rod by an end coupler; and wherein the end coupler is stationary.

7. An apparatus, for treating a bronchial tube having a lumen, which comprises:

a treatment device that comprises at least one radially adjustable electrode;

means for applying force to the at least one radially adjustable electrode to change the diameter of the at least one electrode;

a source of energy;

means for transmitting energy from the source of energy to the at least one electrode;

wherein the treatment device comprises an elongated rod that has a distal end, wherein the at least one radially adjustable electrode comprises a wire that is wound about and along a longitudinal axis of the elongated rod and which has a first end and a second end, wherein the first end is connected to the distal end of the elongated rod; and wherein the means for applying force applies torque that rotates the distal end of the elongated rod.

8. An apparatus, for treating a bronchial tube having a lumen, which comprises:

a treatment device that comprises at least three radially adjustable electrodes;

means for applying force to the at least one radially adjustable electrode to change the diameter of the at least one electrode;

a source of energy;

means for transmitting energy from the source of energy to the at least one electrode; and wherein the treatment device comprises an elongated rod that has a distal end, wherein the at least one radially adjustable electrode comprises a wire that is wound about and along a longitudinal axis of the elongated rod and which has a first end and a second end, wherein the first end is connected to the distal end of the elongated rod.

9. The apparatus of claim 8 wherein said at least three electrodes includes first electrode(s) that are connected to a positive electrode of a RF generator and second electrode(s) that are connected to the negative electrode of the RF generator.

10. The apparatus of claim 8 wherein the first electrode(s) are electrically insulated from the second electrode(s).

11. The apparatus of claim 8 comprising an external electrode and an RF generator having a first RF electrode that is at one polarity and a second RF electrode that is at the opposite polarity and wherein said at least three electrodes are connected to the first electrode and the external electrode is connected to second electrode of the RF generator.

12. The apparatus of claim 1 wherein the source of energy produces energy that is selected from the group consisting of RF energy, alternating current, and microwaves and combinations thereof.

13. The apparatus of claim 1 wherein the source of energy delivers 1 to 25 watts of power.

* * * * *

UNITED STATES PATENT AND TRADEMARK OFFICE
CERTIFICATE OF CORRECTION

PATENT NO. : 5,972,026
DATED : October 26, 1999
INVENTOR(S) : Michael D. Laufer, et. al.

It is certified that error appears in the above-identified patent and that said Letters Patent is hereby corrected as shown below:

Title page, item [75], inventors: delete "Donald" and insert --Don--.

Signed and Sealed this

Twenty-fifth Day of July, 2000

Attest:

Q. TODD DICKINSON

Attesting Officer

Director of Patents and Trademarks